(12) United States Patent
Jin (10) Patent No.: US 9,320,878 B2
(45) Date of Patent: Apr. 26, 2016

(54) PHASE-TRANSITION POLYMERIC MICRONEEDLES

(76) Inventor: Tuo Jin, Shanghai (CN)

(*) Notice: Subject to any disclaimer, the term of this patent is extended or adjusted under 35 U.S.C. 154(b) by 1119 days.

(21) Appl. No.: 13/122,873

(22) PCT Filed: May 12, 2009

(86) PCT No.: PCT/CN2009/000510
§ 371 (c)(1),
(2), (4) Date: Apr. 6, 2011

(87) PCT Pub. No.: WO2010/040271
PCT Pub. Date: Apr. 15, 2010

(65) Prior Publication Data
US 2011/0195124 A1 Aug. 11, 2011

Related U.S. Application Data

(60) Provisional application No. 61/103,560, filed on Oct. 7, 2008.

(51) Int. Cl.
*A61K 9/00* (2006.01)
*A61K 38/00* (2006.01)
(Continued)

(52) U.S. Cl.
CPC .......... *A61M 37/0015* (2013.01); *A61K 9/0021* (2013.01); *A61M 2037/0023* (2013.01); *A61M 2037/0046* (2013.01); *A61M 2037/0053* (2013.01)

(58) Field of Classification Search
None
See application file for complete search history.

(56) References Cited

U.S. PATENT DOCUMENTS

| 2002/0082543 A1 | 6/2002 | Park et al. | |
| 2008/0262444 A1* | 10/2008 | Takada | 604/288 |
| 2008/0269685 A1* | 10/2008 | Singh et al. | 604/173 |

FOREIGN PATENT DOCUMENTS

| CN | 1738710 A | 2/2006 |
| CN | 1899264 A | 1/2007 |

(Continued)

OTHER PUBLICATIONS

Cascone et al., "Hydrogels based on chitosan and dextran as potential drug delivery systems", Journal of Materials Science: Materials in Medicine 10 (1999), 301-307.*

(Continued)

*Primary Examiner* — Ernst V Arnold
*Assistant Examiner* — Jianfeng Song
(74) *Attorney, Agent, or Firm* — Law Offices of Albert Wai-Kit Chan, PLLC (57) ABSTRACT

This invention discloses a novel microneedle system, phase-transition microneedles (PTM), of which the microneedles formed of hydrophilic polymers are swelling but insoluble when absorbing water due to their internal cross-linked network through microcrystalline domains functioning as cross-linking junctions. The microneedles are sufficiently hard to penetrate the epidermis of the skin at dry state, but are converted to hydrogel state to release their loaded cargos by absorbing the body fluid in the dermis layer, and able to be withdrawn from the skin completely (without depositing needle tip materials in the skin) because of their insoluble network. Moreover, formation of the insoluble polymeric network through microcrystalline domains of PTM is achieved by a mild freeze-thaw treatment, for which bioactive agents may be loaded safely in the microneedle tips by adding in the polymer solution prior to molding without denaturing.

9 Claims, 4 Drawing Sheets (51) Int. Cl.
*A61K 39/00* (2006.01)
*A61K 48/00* (2006.01)
*A61K 38/28* (2006.01)
*A61P 3/10* (2006.01)
*A61M 37/00* (2006.01)

(56) References Cited

FOREIGN PATENT DOCUMENTS

| CN | 1986011 A | | 6/2007 |
|---|---|---|---|
| WO | WO-04000389 | * | 12/2003 |
| WO | WO2004062899 A2 | | 7/2004 |
| WO | WO2007/030477 A2 | | 3/2007 |
| WO | WO2007/059289 A1 | | 5/2007 |
| WO | WO2008/096732 A1 | | 8/2008 |
| WO | 2009/040548 | | 4/2009 |

OTHER PUBLICATIONS

PCT International Search Report, Aug. 20, 2009, for Tuo Jin, Int'l Application No. PCT/CN2009/000510, filed May 12, 2009.
Donnelly et al., 2012, "Hydrogel-Forming Microneedle Arrays for Enhanced Transdermal Drug Delivery", Advanced Functional Materials, 4879-4890.
Yu et al., 2015, "Microneedle-array patches loaded with hypoxia-sensitive vesicles provide fast glucose-responsive insulin delivery", Proc. Nat. Acad. Sci., 8260-8265.

* cited by examiner

PHASE-TRANSITION POLYMERIC MICRONEEDLES

CROSS REFERENCE AND RELATED APPLICATIONS

This application is the National Stage of International Application No. PCT/CN2009/000510, filed May 12, 2009, which claims benefit of U.S. Provisional Application No. 61/103,560, filed Oct. 7, 2008. The entire contents and disclosures of the preceding applications are hereby incorporated by reference into this application.

Throughout this application, reference is made to various publications. The disclosures of these publications, in their entireties, are hereby incorporated by reference into this application to more fully describe the state of the art to which this invention pertains.

FIELD OF THE INVENTION

The present invention describes a polymeric microneedle patch which overcomes the limitations of existing microneedles systems and may be used for transdermal delivery system for therapeutics and other applications. The microneedles of this polymeric microneedle array are sufficiently hard and strong to penetrate skin at dry state but turn to hydrogel form when absorb body fluid or water. This system offers sufficient cross-skin permeability and controlled release delivery of hydrophilic agents, including proteins, peptides, DNA, RNA, and other drugs.

BACKGROUND OF THE INVENTION

Non-invasive delivery of protein and peptide therapeutics has been a long-standing objective in pharmaceutical development. Taking diabetes for example, to avoid the life-time long frequent injection, the research efforts for noninvasive routes to replace injection started as earlier as 1921. Since then, many non-injective strategies have been examined, including the inhalation delivery system developed by Pfizer and Nekerta which was withdrawn from the market as soon as commercialization. The recent drop-off of the Pfizer-Nekerta product, Exubera, (together with GlaxoSmithKline's recent failure in developing oral insulin with Nobex) have proven again that to deliver hydrophilic drugs including protein-peptides across our natural biological barriers is a daunting task.

Thanks to the advances in Micro-Electro-Mechanical Systems (MEMS) technology, microneedles, an array of needles several hundreds micron in length, became available. The availability of microneedle array has provided a promising solution for cross-skin drug delivery without pain feeling and skin damage. The needles may penetrate the most impermeable layer of skin (corneum) without hurt the dermis and nerves. Theoretically, a transdermal patch equipped with such an array of the hollow micro-needles to penetrate corneum and with a drug reservoir to store therapeutics may be an idea solution for transdermal delivery of hydrophilic agents. From a practical point of view, however, micro-needle arrays made by MEMS technology are too expensive as a daily disposable dosage form. For extended drug delivery, the metal needles have to be retained in the skin for pro-longed period of time. This may cause skin irritation and delay the recovery of skin punched holes by the needles. In case the needles break and leave metal or other inorganic particles in the skin, more serious skin irritation may be induced. In addition, protein therapeutics stored in the reservoir in solutions state may have stability problem when they are attached on skin at body temperature.

To reduce cost and simplify microneedle fabrication process, arrays with solid needles made of silicon, metals, polymers and sugars were used for transdermal delivery of drugs. A solid microneedle array was used to punch microholes on the skin first, then drug solutions were dropped on the punching site immediately after the microneedle array was removed. The punch-drop type of drug administration is, however, compromised with lack of control in dose and skin up-take of the drug. The holes punched by the microneedle array may close after removing of the needles so that drug diffusion across the skin may be terminated as incident.

Fabricating microneedle arrays using polymeric materials such as polylactic acid (PLA), polyglycolic acid (PGA), poly-lacitc-co-glycolic acid (PLGA), cellulose, amylopectin, maltose, cross-linked polyvinyl pyrrolidone (PVP) is a reasonable strategy to improve biocompatibility of the patch. These systems, however, are still incapable to offer a sustained or controlled release drug delivery. Microneedle arrays made of PLA, PGA or PLGA may contain no drug and are used in the same way as the solid metal needles: to punch microholes on the skin, followed by spreading drug solutions on the punching site. The problem by incident closing of the microholes remains. These microneedle array systems may also be fabricated with drug load in the matrix of needles. Drugs may be release subcutaneously by gradual degradation of the polymer of which microneedles are formed. However, degradation of PLA, PGA and PLGA is often too slow to deliver drug at required rate. In addition, loading proteins in a hydrophobic matrix may cause the macromolecules to denature. Furthermore, after degradation of the microneedles (made of the degradable polymers), the trans-corneum channels will no long exist so that only the drugs loaded in the needle matrix have the chance to be delivered.

Microneedle arrays made of cellulose, amylopectin, maltose cross-linked PVP are water soluble and contain drugs in the body of the needles. Drugs are delivered when the microneedles are dissolved by body fluid. This type of microneedle arrays offer a well-defined dose of drug, but are not able for a sustained or controlled delivery over a prolonged period of time since the holes may close after the needles are dissolved. There has yet to be a microneedle array system that provides sustained and controlled transdermal drug delivery to date.

SUMMARY OF THE INVENTION

The microneedle system in this invention is formed of hydrophilic polymeric materials which are hard and strong enough to penetrate epidermis at dry glassy state, but undergoes a phase-transition to hydrogel state by absorbing body fluid when contact with dermis. This transdermal patch consists of a microneedle array and a drug reservoir plate (called "holding plate" bellow) on top of which the microneedles stand as an array (as an integrated piece). Therapeutics and other agents to be delivered can be loaded in the matrix of the needles and the reservoir plate, or loaded only in the needles.

Figure 1:
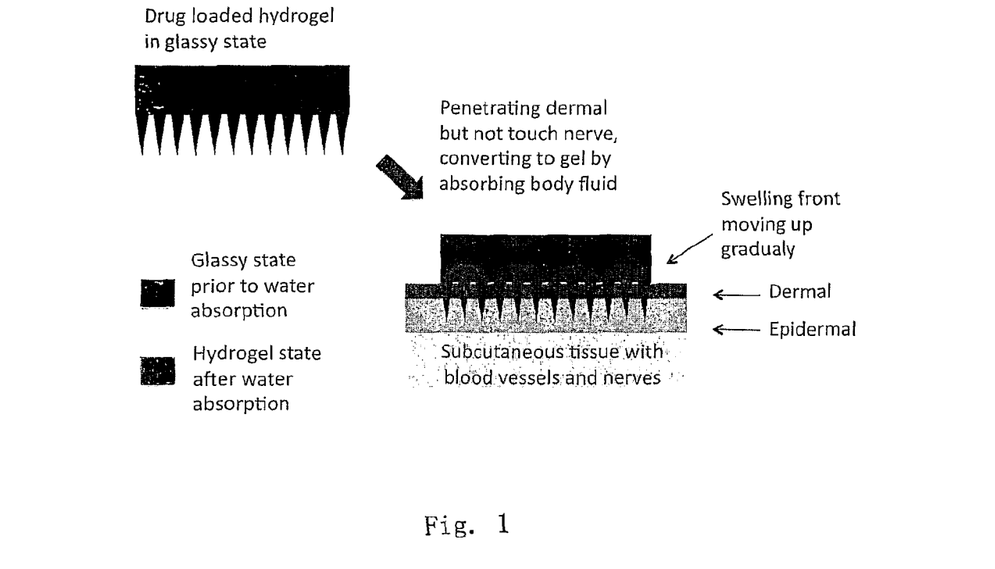
FIG. 1. Schematic illustration of the working mechanism of phase-transition microneedle system.

The working mechanism of the phase-transition microneedle system is illustrated in FIG. 1. The microneedles formed of the hydrophilic polymers penetrate the epidermis, then absorb body fluid to be hydrated to hydrogel state permeable to proteins, peptides, genes or other water soluble therapeutics loaded in the matrix of the needles and/or the reservoir plate. During the phase transition of the needles and the plate from dry state to hydrated gel state, diffusion channels for the lipophobic agents loaded in the system are opened (formed). This microneedle system differs from that made of polysaccharide in that the microneedles do not disappear by hydration, but remain in the skin as sustained diffusion channels. Controlled release delivery is achieved by three factors: polymer phase transition, drug diffusion, as well as the fabrication process of the microneedle patch (programmed casting).

Figure 2:
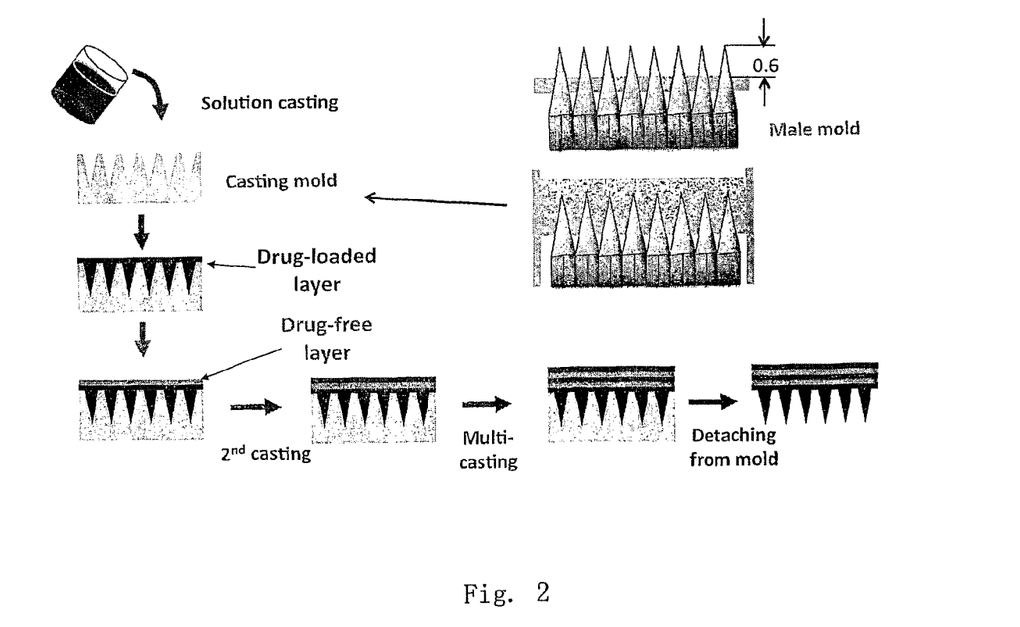
FIG. 2. Schematic description of microneedle fabrication process using programmed casting method.

In addition to the phase transition nature, one important advantage of this microneedle array system is its easy yet multi-functional fabrication process. The microneedle array can simply be prepared by casting an aqueous solution of the microneedle-forming polymer on a mold having microholes aligned on its surface as an array. The final form of the microneedle patch is formed by drying the casted solution and detached it from the mold. Drugs to be delivered are added into the polymer solution before casting on the mold. A unique and interesting feature of this system is that its fabrication process can be used to achieve a desired release pattern. By a programmed casting (i.e. casting polymer solutions with different drug concentration stepwise on the mold), a precisely programmed drug release profile can be achieved. FIG. 2 describes the process of programmed casting schematically.

For example, a polymer solution loaded with drug is first casted on the microholes-aligned mold to form a microneedle-holding layer. Then a drug-free (or drug-reduced) polymer solution is casted on top of the first layer. This drug-loading and drug-free (or drug-reducing) casting may be repeated for several times, by which a programmed multi-pulse release profile can be attained. In this case, the peak height of each pulse can be determined by the concentration of the drug in the respective polymer solution, peak width of each pulse is decided by the thickness of respective polymer layer, and the peak interval is controlled by the thickness of the drug-free (or drug-reduced) layer. To achieve a linear (zero-order) release, the drug concentration is gradually increased during the programmed casting.

The programmed casting technology may also allow us to prepare microneedle patches with hard needles and soft holding plate (even at dry state) by using different polymer solutions for respective layers of casting. This type patched may be preferred for skin care applications because the patches may fit the contours (outlines) of human faces.

DETAILED DESCRIPTION OF THE INVENTION

Selecting Polymeric Materials

Selecting the microneedle-forming polymer or polymers is the first step to prepare phase transition microneedle patch. The polymer must be soluble in water before the patch is formed in order to add the drugs in its aqueous solution and cast on a mold. Also, the polymeric materials must not be soluble by water after the patch is formed so that the microneedles penetrated skin can retain their shape and create sustained diffusion channels for the agents to be delivered. Of course, the materials must be hard and strong enough at dry state to penetrate dermis and able to swell when contacting body fluid to open the diffusion channels for drugs.

The materials that meet the above-mentioned criteria are those which are hydrophilic and soluble in water under certain condition (hot water for example) but form water-insoluble hydrogel network hereafter. There are two ways to form hydrogel network, by chemical cross-linking, or by physical cross-linking. To prepare chemically cross-linked hydrogel mironeedles, one feasible method is to modify polysaccharides with reactive groups and cross-link the reactive groups after the polysaccharide solution is casted on the mold. For physically cross-linked hydrogel microneedles, two mechanisms may be used, ionic interaction and microcrystal formation. For the ionic interaction mechanism, polysaccharide processing charged groups is allowed to interact with multivalent counter ions in aqueous solution system. For the mechanism via microcrystal formation, water-soluble polymers able to form microcrystalline domain should be used.

The polymeric materials used to form the microneedle patch have been used in the pharmaceutical field for years and have proven compatibility with the skin and with proteins.

As an example in the present invention, polyvinyl alcohol (PVA) was used to form microneedle patches. PVA is soluble in hot water but forms hydrogel when its aqueous solution is frozen and thawed. The more cycles the PVA solution undergoes, the more mirocrystalline domains (which function as cross-link junctions of hydrogel network) are formed.

Another important criterion for phase-transition is hardness. PVA is tough to being broken but may not be hard enough to penetrate skin. PVA turns to be plastic when the environment temperature is more than 25° C. This problem can be easily resolved by mixing PVA with polysaccharide, for example dextran, alginate, hyaluronic acid, chitosan or cellulose. However, since polysaccharides, such as dextran, are soluble in water, the content of polysaccharide mixed in PVA matrix should be limited (below 25% by weight) in order to maintain the hydrogel network and needle shape when contacting with body fluid.

Designing of Microneedle Patches

The present invention has also disclosed several signs of microneedle patches. For controlled-release transdermal delivery of sufficient dose, the patch detached from the mold should consist of a microneedle array and a drug reservoir plate (the "holding plate" as an integrated piece with the microneedle array), with the microneedle array itself as part of the drug reservoir. Once applied onto skin, the polymeric microneedles penetrate stratum corneum, and the integrated patch absorb body fluid and gradually swell upwards from the bottom to form sustained diffusion channels for loaded therapeutics. The swelling process itself will be part of the mechanism (together with drug diffusion) of controlled-release delivery of the loaded proteins, peptides or other therapeutics.

The rate of drug release for a given drug from the transdermal patch can be adjusted by the density of cross-link junctions of the hydrogel matrix and the sizes of the diffusion channels formed by hydration. These two important criteria may be achieved by patch forming process and patch composition. For the PVA-dextran patch examined in this invention, the more cycles of the freeze-thaw treatment the higher population of the cross-link junctions will be formed; the more content of dextran mixed into the PVA matrix, the larger diffusion channels may be formed.

To achieve programmed multi-pulse release, a programmed casting process is feasible. The aqueous polymer solutions loaded with various concentrations of a given drug may be casted on a microneedle-forming mold (casting mold) stepwise and in a well designed program, so that the release profile can be precisely designed.

To reach a linear (zero order) release profile, a (drug) concentration-gradient casting will be carried out. In brief, the casting will be stepwise in such an order from the polymer solutions loaded with lower concentration of a given drug to that with higher concentration drug.

For the biological therapeutics over 10K in molecular weight, the sizes of the diffusion channels of the hydrogel matrix may not be sufficient large. In this case, the macromolecular therapeutics will be mainly loaded in the microneedle part (i.e. the microneedles will be the main drug reservoir).

This microneedle technology may also be used as cosmetic membranes. In this case, the patch is designed in such a way that the microneedles are hard but the holding plate is soft in order to fit the outline (contours) of human faces. As an example for this invention, PEG (or glycerol) instead of polysaccharides will be mixed in the PVA matrix of the holding plate.

Casting Process and Mold Design

An acceptable and workable casting process for fabricating our phase-transition microneedle patch must ensure two objectives: 1) having the viscous polymer solution full-filled the microholes of the casting mold; 2) drying the casted microneedle patch without collapse and deformation of the needles. In the present invention, the two goals will be achieved by rational designs of the casting process and the casting mold. To enable the polymeric solution (a polymer solution is normally viscous) to fill into the microholes, a force should be applied. Two forces are conceivable: centrifugation force and hydrostatic pressure. From a manufacturing purpose, the later is more affordable and easier to scale up. On the other hand, to avoid needle collapse and deformation, the drying process must ensure the drying-induce collapse not occur to the needles (but may be to the holding plate). In another word, water evaporation should start from the needles so that the needles may be hardened before the holding plate.

The mold design has to meet the process requirements discussed above. To force the hydrophilic polymer solution to full fill the microholes, the mold materials (or the microholes) should be permeable to air to avoid air trapping in the microholes during casting. The air permeability may also allow application of a vacuum at the back side of the mold to suck the polymer solution into the microholes (i.e. to create a hydrostatic force to force the solution into the holes). On the other hand, the mold should not leak liquid solution so that the ingredients to form the patch will not be lost into the pores of the mold materials. The surface property of the mold material, especially the surface of the microholes which contacts with the microneedle-forming polymer solution, should be hydrophilic to allow good contact with the aqueous polymer solution. However, the contact should not be to adhesive so that the dried microneedles may easily detach from the mold. As an example, ceramic materials and gypsum are used to form the mold in the present invention.

Packaging of Phase-Transition Microneedle Patch

Since water induce phase transition (from hard xerogel to soft hydrogel) is involved in the working mechanism of the microneedle patch, water-prove packaging is an important step for fabrication of the system to avoid softening of the microneedles by absorbing moisture. Another function of packaging is to protect the sharp tip of the microneedles. The packaging for the microneedle patch involves a water-prove back which has a skin adhesive surrounding to touch to the skin, a thin Teflon membrane which is penetrated by the microneedles and closely contact with the surface of the holding plate, a layer of sponge to which the microneedles insert, and another water-prove membrane on the top of the sponge to seal the patch from absorbing moisture. Prior to application, the top membrane and the sponge layer are removed.

Applications of Phase-Transition Microneedle Patch

The phase transition microneedle patch developed in this invention may be used for transdermal delivery of variety of therapeutics including protein and peptide drugs, genes and RNA, subunit vaccines, and cosmetic agents. Proteins and peptides able to be delivered through transdermal route using the phase-transition microneedles patch are any of those less than 200K in molecular weight, such as insulin, calcitonin, erythropoietin (EPO), exanatide, GLP-1, GM-CSF, interferon, factor VIII, interleukins, HSF, PEGylated Recombinant Human Interferon-alpha 2b (PEG-IFNα2b), Recombinant Human Interferon (IFN), Recombinant Human Parathyroid Hormone (PTH1-84), Recombinant Human soluble CD40 (CD154) Ligand/TRAP, Recombinant Human Bone Morphogenetic Protein (BMP), Recombinant human Interleukin-15 (IL-15), Recombinant Human Leukemia Inhibitory Factor (LIF), Recombinant Human Interleukin-2 (IL-2), Recombinant human growth hormone (rHGH), Epidermal Growth Factor (EGF), Basic fibroblast growing factor (FGF), Transforming growth factor beta 1 (TGF-β1), IGF, Recombinant Human Vascular Endothelial Growth Factor (VEGF), PDGF, Endothelial Cell Growth Factor (ECGF), NGF, BDGF, Brain-derived growth factor A (BDGF-A), tissue polypeptide antigen (TPA), antibody, Coagulation Factor VIII, Hereditary factor IX, Human Immunoglobulin, stem cell factors (SDFs), activated protein C and so forth. Subunit vaccines able to be delivered using this system are any of those less than 500K in molecular weight. Gene and RNA able to be delivered using this system are those which are formed as nanoparticles or as free molecules.

For cosmetic applications, the patch may be designed in such a way: the microneedles are hard at dry state, but the holding plate is soft in order to fit the contour of human faces. The materials to form the hard microneedles are the same as the patch for therapeutic applications, while the holding plate contains some softening materials such as liquid PEG or glycerol. For delivery of extremely large molecules (i.e. those over 100K in molecular weight), the agent to be delivered should be mainly loaded in the matrix of the microneedles rather than the holding plate.

EXAMPLES

The examples below provide comprehensible description to help technical workers familiar with the general knowledge and methods to better understand the art of the present invention. The examples should not be used to limit the scope of this invention and its applications.

Example 1

Figure 3:
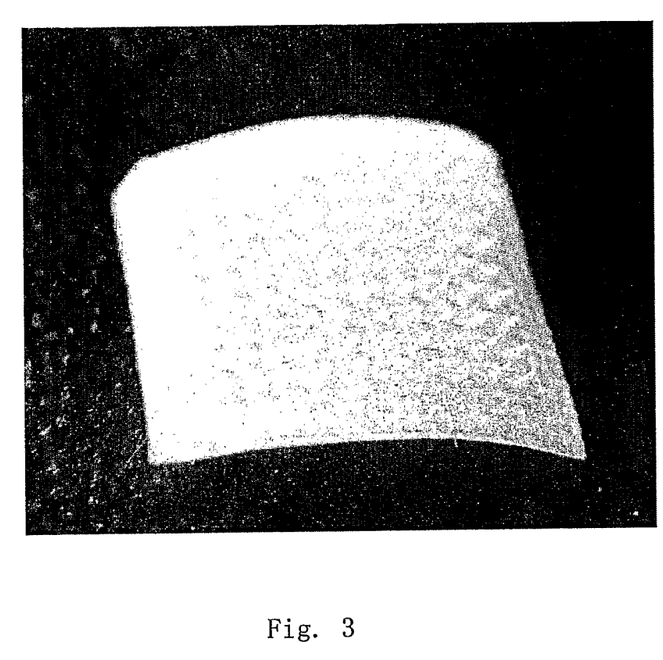
FIG. 3. Photo image of a microneedle patch prepared by casting a mixed solution of PVA and dextran on a mold made of gypsum.

Preparation of Phase-Transition Microneedle Patch Using Polyvinyl Alcohol (PVA) and Dextran A mixed aqueous solution of PVA (15% by weight in concentration and 10,000-250,000 in weight-average molecular weight) and dextran (0-3% by weight in concentration and 6,000-5,000,000 in weight-average molecular weight) was casted on a gypsum mold consisting of an array of microholes. After casting the polymer solution on the mold, vacuum was applied on the other side of the mold to suck the polymer solution into the microholes. Drugs to be delivered (such as insulin) were added in the mixed polymer solution before casting onto the mold. After filling the microholes with the polymer solution, the sample was cooled to freeze the water-based solution. The sample may be frozen again after it is warmed up to room temperature and the freeze-thaw treatment may be repeated several time to adjust the density of the crystalline cross-linking junctions of PVA. Then, the top surface of the polymer was covered to retard water evaporation rate from the top, and vacuum was continuously applied underneath of the mold to ensure that the microneedles were dried before the holding plate. Even if the system was collapsed, the collapse occurred downwards from the holding plate to the needles. Finally, the dried microneedle patch was detached from the mold and sealed with water-prove materials. FIG. 3 shows a photo image of a microneedle patch detached from a mold.

Figure 4:
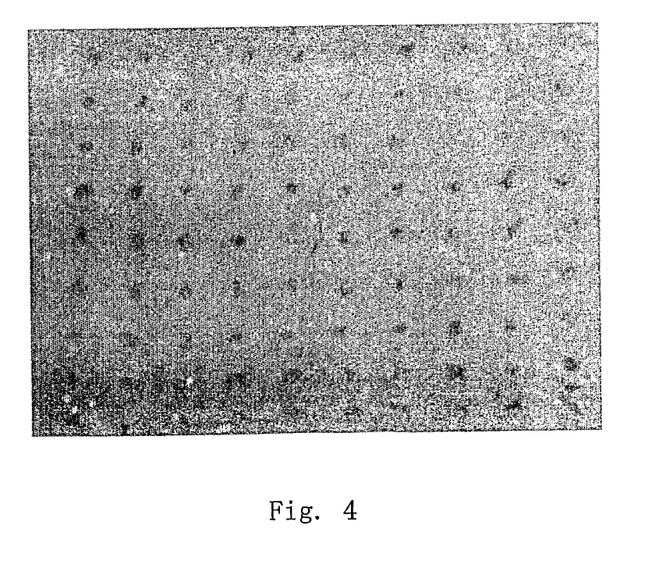
FIG. 4, Photo image of a piece of pig skin punched by a dyed (by Trypan Blue) microneedle patch of PVA and dextran.

The microneedles patch detached from the mold as above was applied on a piece of hair-removed pig skin to test its ability to penetrate skin. Prior to apply the patch on the skin, the microneedles were dyed with Trypan Blue. FIG. 4 shows the photo image of the pig skin right after being patched by the dyed microneedle patch. The colored holes clearly indicated that the microneeldes penetrated the skin.

Concentration of the polymer solution is an important variable in terms of optimization of the casting process of the microneedle patch. Since volume reduction due to dehydration is the main cause for collapse of the microneedles patch, higher concentration is preferred for preventing or limiting deformation of the microneedles during the drying step. However, a polymer solution of high concentration is more viscous so that filling into the microholes of the mold becomes challenging. Polymer solutions of low concentration, on the other hand, is easier to fill in the microholes but volume collapse due to dehydration becomes more significant. To determine the concentration limit, the PVA solutions from 5% to 30% weight concentration were examined. The results are summarized in the table bellow.

Example 2

Release Kinetics of Insulin from Microneedle Patches

To test release profiles of insulin, the microneedle patches prepared as above were attached to a model skin mounted on a Franz diffusion cell filled with PBS buffer at pH 7.4 being stirred at 100 rpm (as the receiving pool). The patch was covered with plastic film to prevent water evaporation from the top. Release kinetics of insulin from the patch was examined at 37° C. by assaying the insulin concentration change in the PBS buffer. Sample was taken from the receiving cell at a programmed time and assayed for insulin concentration using HPLC. Profiles of the cumulative release of insulin from the phase-transition microneedle patches formed via various cycles of freeze-thaw treatment and formed of PVA and dextran at various ratio are shown in FIG. 5 and FIG. 6, respectively.

Figure 5:
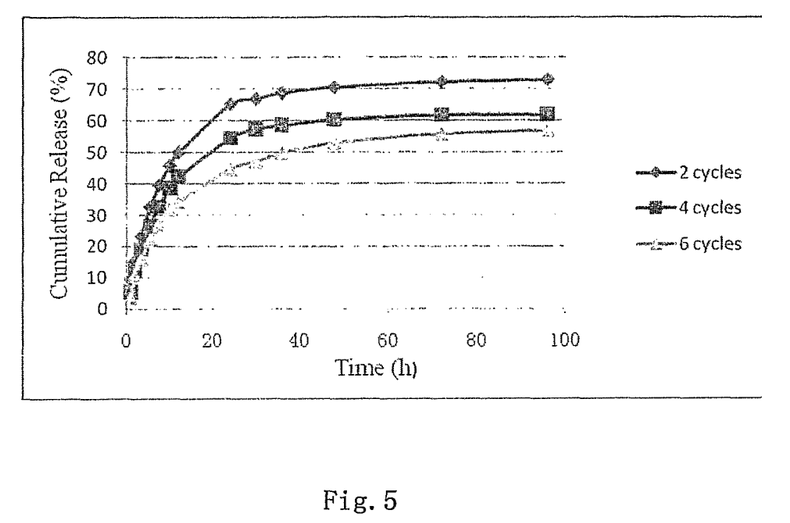
FIG. 5. Profiles of cumulative release of insulin from microneedle patches formed of PVA and dextran (PVA/dextran=80/20) via various cycles of freeze-thaw.
Figure 6:
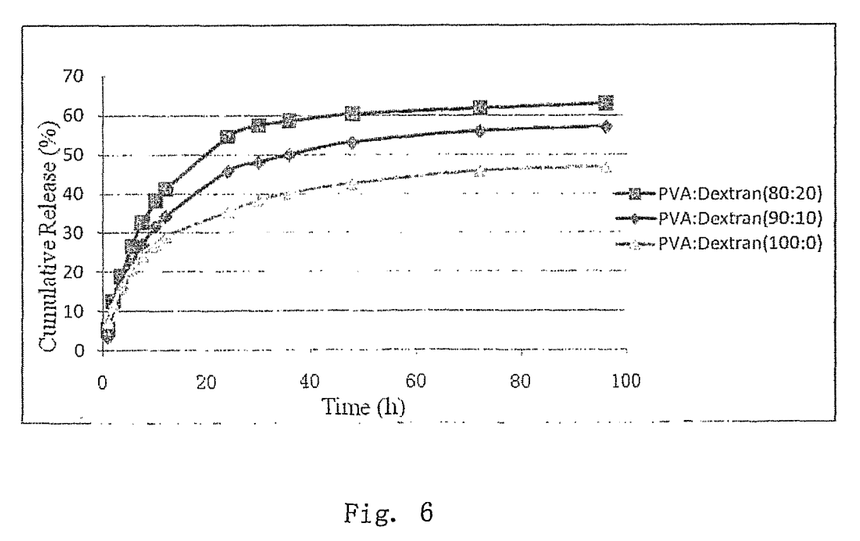
FIG. 6. Profiles of cumulative release of insulin from microneedle patches formed of PVA and dextran undergone 4 cycles of freeze-thaw treatments treatment but different in PVA/dextran ratios.

FIG. 5 shows the cumulative release profiles of the patches prepared at fixed PVA/dextran weight ratio (80/20) and varied freeze-thaw cycles (2, 4 and 6). For the patches prepared via 2 and 4 freeze-thaw cycles, insulin release was stopped at 40 hours since the experiment. However, 70% of total insulin loading was released from the former and 60% from the later. FIG. 6 shows release profiles of the patches prepared via fixed freeze-thaw cycles (4 cycles) and varied PVA/dextran weight ratios (100/0, 90/10 and 80/20). The rate and extent of insulin release was increased as the dextran content was increased.

Example 3

Preparation of Layered Phase-Transition Microneedle Patches Via Programmed Casting (Molding)

Two methods were used to prepare layered phase-transition microneedle patches: repeated casting and assembling of pre-formed sheets. For whatever the method, the layer of microneedle array formed by casting a polymer solution on the mold having an array of microholes. For the repeated-casting method, a layer of drug-free solution (or drug-reduced solution) was casted on the top of the first layer after the freezing treatment (some time the freezing step was omitted). This operation was repeated several times till the designed structure was achieved. FIG. 2 shows the fabrication process schematically. The drug concentration and thickness of each layer may be varied to achieve designed release profiles.

For the assembly method (not shown by figures), after the drug-free or drug-reduced solution was casted on the top of the layer of microneedle array, a pre-formed drug-loaded PVA-dextran sheet was placed on the newly casted layer. Then the drug-free or drug-reduced solution was casted again on the top of the sheet, followed by assembly of another pre-formed sheet. This operation may be repeated till

TABLE 1

Effect of polymer concentration on casting process of microneedle patches

| PVA conc. | 5% | 10% | 15% | 20% | 25% | 30% |
|---|---|---|---|---|---|---|
| Dext. conc. | 0.6% | 1.3% | 2% | 2.5% | 3% | 4% |
| Solubilization | readily | readily | by heating | by heating | by heating | difficult |
| Mold filling | easy | easy | enforced | enforced | enforced | difficult |
| Collapse ratio | large | large | acceptable | acceptable | good | N/A |
| Conclusion | N/A | acceptable | recomment | recomment | acceptable | N/A | designed structure is assembled. The two methods have no significant differences in release profiles of drugs.

Example 4

Figure 7:
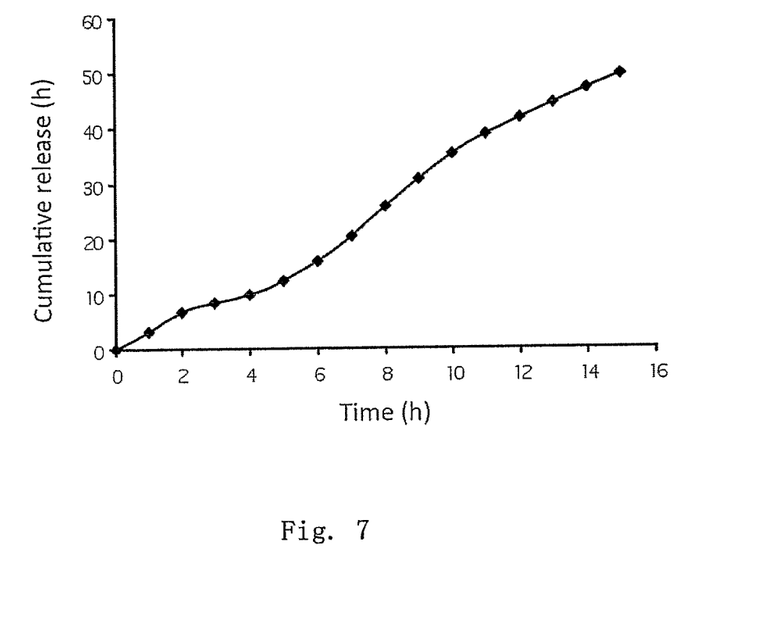
FIG. 7. Profile of cumulative release of insulin from microneedle patches formed of PVA and dextran (PVA/dextran=80/20) prepared by three layers of programmed casting (drug-loaded+drug-free+drug-loaded).
Figure 8:
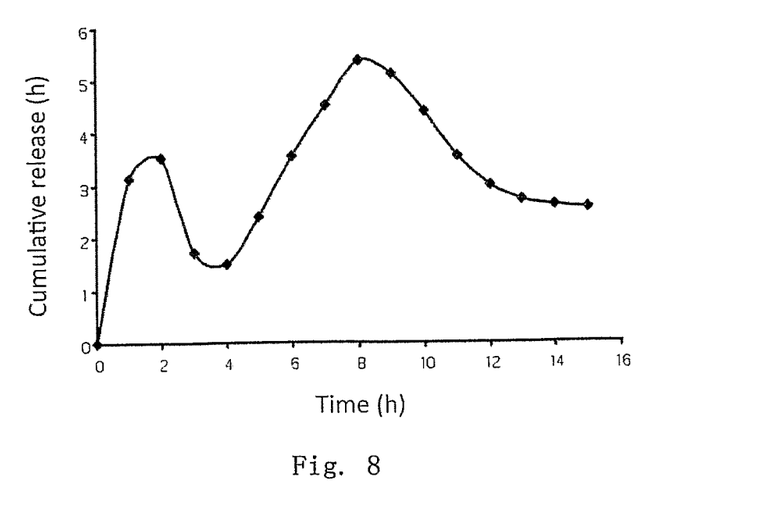
FIG. 8. Profile of hourly release of insulin from microneedle patches formed of PVA and dextran (PVA/dextran=80/20) prepared by three layers of programmed casting (drug-loaded+drug-free+drug-loaded).

Insulin Release Profiles from Phase-Transition Microneedle Patches Prepared by Programmed Casting The microneedle patches prepared by programmed casting were examined using the procedure descript in Example 2. FIG. 7 and FIG. 8 show a cumulative release profile and an hourly release profile of insulin from a three-layer (drug-loaded+drug-free+drug-loaded) microneedle patch, respectively. The PVA/dextran weight ratio of the patch was 85/15, and the insulin content in the drug-loaded layer was 1% by weight. Clearly, the designed profile (two insulin release peaks with five hours interval) were achieved by the programmed casting.

Example 5

Preparation of Phase-Transition Microneedle Patches Consisting of Hard Needles and Soft Holding Plate In order to fit the contour of human faces, PVA solution mixed with PEG (100-1,000 in weight-average molecular weight) or glycerol was used to cast the holding plate. First, a mixed solution of PVA and dextran was casted on the mold to for the layer having the microneedle array. After the sample was subjected to a freezing treatment, another polymer solution containing PVA and PEG-600 (or glycerol) was casted on the top of the first layer, followed by the drying process as Example 1. The patch detached from the mold was confirmed (by touching the patch with hands) to have hard needles and soft holding plate (data not shown).

What is claimed is:

1. A microneedle patch formed of hydrophilic polymeric materials, comprising a microneedle array and a plate wherein the microneedles are standing and aligned on, wherein the polymeric materials are the combination of polyvinyl alcohol (PVA) and polysaccharide or the combination of polyvinyl alcohol (PVA) and polyethylene glycol (PEG), wherein the polymeric materials are crosslinked, and wherein:
   a) the microneedle tips of the patch are water-swellable but water-insoluble; and
   b) the matrix of the microneedles is structured as a polymeric network with microcrystalline domains as the cross-linking junctions.

2. The microneedle patch of claim 1, wherein the polysaccharide is selected from dextran, alginate, hyaluronic acid, chitosan and celluloses.

3. The microneedle patch of claim 1, wherein at least one bioactive agent selected from proteins, peptides, subunit vaccines, DNA, RNA, lipophobic therapeutics, drug-bearing liposomes, drug-bearing nanoparticles, and a mixture of any of the above agents is loaded in the hydrophilic polymeric materials.

4. The microneedle patch of claim 3, wherein the proteins and peptides are selected from insulin, calcitonin, exenatide, GLP-1, HSF, GM-CSF, erythropoietin (EPO), interferon, PEGylated interferon, factor VIII, factor IX, interleukines, IL-2, IL-15, hGH, PTH, BMP, FGF, TGF-$\beta$1, IGF, VEGF, PDGF, ECGF, NGF, BDGF, BDGF-A, TPA, SDFs and activated protein C.

5. The microneedle patch of claim 3, wherein at least one biologic agent can be loaded in the microneedles of polymeric materials or loaded in the microneedles and the plate.

6. The microneedle patch of claim 5, wherein the polymeric materials are the combination of polyvinyl alcohol (PVA) and polysaccharide(s).

7. The microneedle patch of claim 1, wherein the polysaccharide(s) is selected from dextran, chitosan, alginate and hyaluronate.

8. The microneedle patch of claim 7, wherein chitosan, alginate and hyaluronate are each independently in a salt form, free base form (chitosan), or free acid form (alginate and hyaluronate).

9. The microneedle patch of claim 7, wherein the weight-average molecular weight is 10,000-250,000 for PVA; 6,000-5,000,000 for dextran; 20,000-4,000,000 for chitosan; 10,000-3,000,000 for alginate; 100,000-5,000,000 for hyaluronate; and 100-1,000 for PEG.

* * * * *